United States Patent [19]

Maganias

[11] Patent Number: 4,802,493

[45] Date of Patent: * Feb. 7, 1989

[54] DEVICE AND METHOD FOR ALLERGY TESTING

[76] Inventor: Nicholas H. Maganias, Reston Medical Bldg., 1712 Club House Rd., Reston, Va. 22090

[*] Notice: The portion of the term of this patent subsequent to Sep. 25, 2001 has been disclaimed.

[21] Appl. No.: 16,487

[22] Filed: Feb. 17, 1987

Related U.S. Application Data

[63] Continuation of Ser. No. 779,612, Sep. 25, 1985, abandoned, which is a continuation of Ser. No. 445,746, Nov. 30, 1982, abandoned, which is a continuation-in-part of Ser. No. 330,587, Dec. 14, 1981, Pat. No. 4,473,083.

[51] Int. Cl.$^4$ ............................................. A61B 5/04
[52] U.S. Cl. ............................................. 128/743
[58] Field of Search .................. 128/743; 604/46, 43

[56] References Cited

U.S. PATENT DOCUMENTS

| | | | |
|---|---|---|---|
| Re. 25,637 | 9/1964 | Kravitz et al. | 128/743 |
| 2,304,817 | 12/1942 | Grozin | 128/743 |
| 2,893,392 | 7/1959 | Wagner et al. | 128/743 |
| 3,072,122 | 1/1963 | Rosenthal | 604/46 |
| 3,136,314 | 6/1964 | Kravitz | 604/46 |
| 3,556,080 | 1/1971 | Hein | 128/743 |
| 3,814,097 | 6/1974 | Ganderton et al. | 128/743 X |
| 4,090,752 | 5/1978 | Long | 128/641 |
| 4,304,241 | 12/1981 | Brennan | 128/743 |

*Primary Examiner*—Edward M. Coven
*Attorney, Agent, or Firm*—Cushman, Darby & Cushman

[57] ABSTRACT

A method for allergy testing is carried out by: applying to the skin of a patient test strip formed of a thin, flexible strip of adhesive tape a portion of which carries on its adhesive side at least one skin-penetrating lance carrying an allergen; pressing the test strip against the skin to cause temporary adhesion of the strip to the skin and to cause the lance to penetrate the skin to a depth less than the subcutaneous tissue thereby carrying the allergen into the skin and maintaining contact between the allergen and the thus-traumatized skin cells; and leaving the strip in place for a period of time sufficient for the patient's skin, if allergic to the allergen, to produce a visible allergic reaction. The test strip may be transparent so that the skin reaction can be observed through the strip. The strip may include a plurality of closely-spaced lances or a single lance.

19 Claims, 2 Drawing Sheets

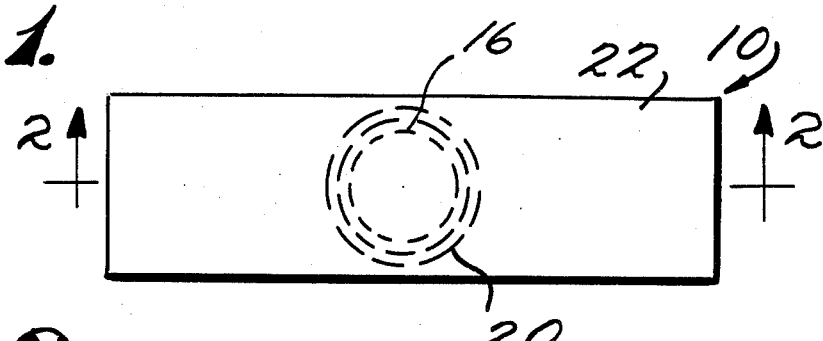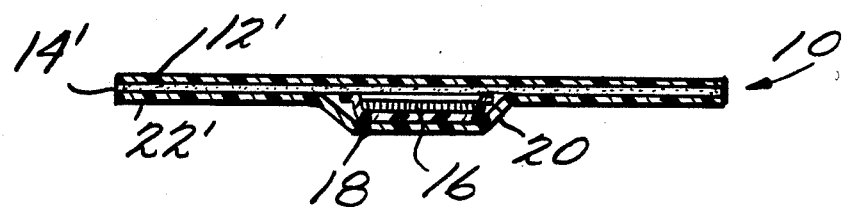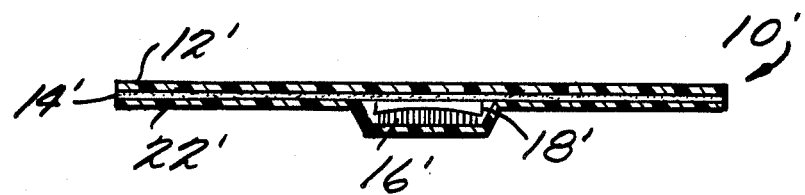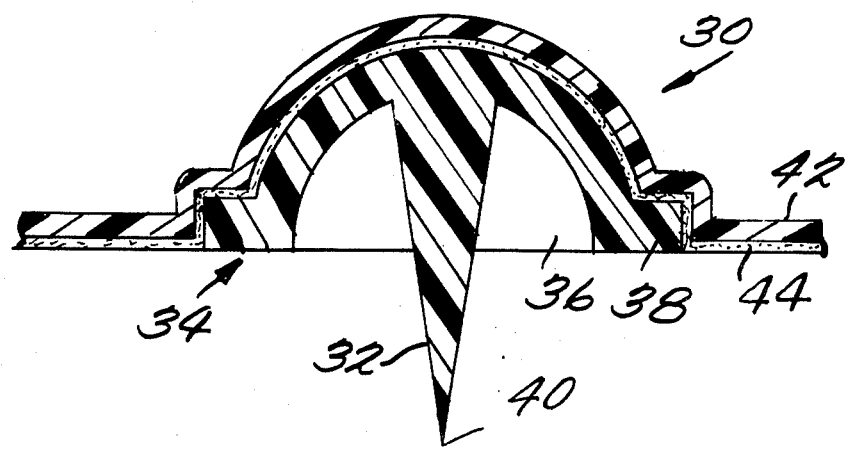

DEVICE AND METHOD FOR ALLERGY TESTING

This application is a continuation of Ser. No. 779,612 filed Sept. 25, 1985 (now abandoned), which was a continuation of Ser. No. 445,746 filed Nov. 30, 1982 (now abandoned), which was a continuation-in-part of Ser. No. 330,587 filed Dec. 14, 1981, now U.S. Pat. No. 4,473,083.

This invention relates to a method and device for allergy testing the skin of a patient.

BACKGROUND

Testing the skin of a patient for an allergic reaction to any of a variety of allergens is a known technique involving penetration of the allergen into a small area of the skin and subsequently visually observing the reaction, if any, of the skin to the allergen. Known procedures for applying the allergen include the scratch test, the prick test and the intradermal test. The scratch test is carried out by applying a few drops of the allergen to the skin and slightly abrading the skin by scratching at that location. The prick test is similar except that abrasion of the skin is effected by making a plurality of pricks with a sharp needle. The intradermal test is carried out by injecting the allergen into the skin.

U.S. patents relating to the introduction of biochemical substances into the skin include Krug et al. U.S. Pat. No. 3,289,670; Kravitz et al. U.S. Pat. Nos. Re. 25,637, 2,817,336, 3,062,212, 3,136,314 and 3,351,059; Wager et al. U.S. Pat. No. 2,893,392, Ganderton et al. U.S. Pat. No. 3,814,097 and Gerstel et al U.S. Pat. No. 3,964,482.

SUMMARY OF THE INVENTION

The present invention is based in part on the observation that each of the scratch test, the prick test and the intradermal test has one or more disadvantages. The scratch test may not produce enough scarification of the skin and thus lead to an inaccurate conclusion due to insufficient skin cell damage to permit adequate entry of and reaction with the allergen. The prick test may produce excessive trauma, for example, microbleeding, which can produce histamine release thereby confusing the results of the test. With the intradermal test it is frequently difficult to titrate the degree of skin reaction and large and often false positive reactions develop. Each procedure has its own advantages, however. The medical practitioner will generally decide on which procedure to use taking into consideration the time required for the test, pain inflicted on the patient, trauma to the skin, weak reactions, expense and other features.

The present invention provides an allergy testing method, and a disposable device for use in carrying out the method, which combines a number of the advantages of the usual procedures while avoiding or reducing the disadvantages referred to above. The method involves applying to the skin of the patient a test strip in the form of a thin flexible piece of adhesive tape a portion of which carries on its adhesive side one or more projecting lances coated with or supplied with the allergen and capable of piercing the skin to a limited degree. The test strip, and in particular the portion carrying the lance or lances, is then pressed against the skin to cause the lance or lances to penetrate the skin to a depth less than the subcutaneous tissue thereby carrying some of the allergen into the skin and maintaining constant contact between the allergen and the traumatized skin cells. After a period of time appropriate for the skin to react with the allergen, for example 15 to 20 minutes, the test strip including the lance or lances is removed from the skin and discarded. The degree of skin reaction, in terms of inflammation, swelling or the formation of protuberances, and hence the degree of allergy is then determined by the medical practitioner by visually observing the area of skin which was punctured by the lance or lances. Several such tapes, each carrying a different allergen, can be applied to the skin simultaneously or essentially simultaneously. Alternatively a single tape can carry a plurality of lances or groups of lances, each lance or group carrying a different allergen. The appearance of the skin area may be compared to one or more control skin areas which have been similarly punctured by similar test strips having a lance or lances free of allergen.

The lance or lances, which may be made of plastics material or metal, may be needle-like with sharp points, conical with sharp points or blade-like with both edges sharpened and a pointed end or rounded knife-edge end. In one embodiment there is at least one group of closely-spaced short needle-like lances, the group being for example circular and having a diameter less than the smallest dimension of the adhesive surface of the strip. A suitable arrangement is 5 to 10 lances disposed in a circular group of approximately 0.125 inch diameter. The length of the lances may be in the range 0.06 inch to 0.03 inch.

In another embodiment the test strip may carry a single lance or several rather widely spaced-apart lances. In this case the single lance should be more massive than the smaller lances used in the plural-lance embodiment in order to provide the necessary skin damage. A suitable shape for such a lance is conical with a sharp point. An advantage of the single lance construction is that the single lance will provide better penetration as well as more damage to the skin cells with resulting better allergic reaction. A single lance can also provide better attachment to the skin for longer application periods.

The preferred shape of the strip is rectangular, somewhat smaller than the conventional adhesive bandage applied to minor cuts and scratches, although square, circular, oblong or other shapes are satisfactory. It has been found that test strips of this kind when used as described above do not produce excessive trauma or microbleeding, while at the same time they produce reliable test results due in part to the fact that they maintain constant contact between the allergen and the traumatized skin cells during the test.

The test strip and the adhesive material are made of low allergenic material. Also, the strip should be colorless and transparent so that the reaction of the skin can be observed through the strip and so that, in the event of over-reaction, the test can be interupted by removing the strip from the skin. The adhesive area of the strip will always be sufficiently great to adhere well to the skin.

The allergen initially applied to the lances may be in liquid form or solid form. With a plural-lance test strip a liquid allergen can be impregnated into and retained in the interstices between the lances. If the allergen is dry, distilled water may be added shortly before use to dissolve or disperse the allergen and allow impregnation. With a single-lance test strip it is preferable that the lance project from a cavity in a substrate and to retain the allergen, liquid or initially dry, in the cavity so that it will be supplied to the lance. In either case the lance or lances may be covered with a removable protective cover to exclude air and dust and to maintain the lances in sterile condition until ready for use. The cover may be a plastic film overlying the lance or lances only or overlying the lances and the layer of adhesive. The allergen may of course by any allergen, such as those typically used for testing allergy to trees, grasses, weeds, cat hair, dog epithelium, house dust, molds, spores and certain inhalents.

The lance or lances may be held in their relative positions by having their inner ends secured to a substrate which in turn is attached to the adhesive tape. The substrate may be flexible or rigid and may be attached to the adhesive tape by means of the same layer of adhesive which adheres the tape to the patient's skin. The substrate can be concave so as to provide an outwardly facing cavity for retaining the liquid allergen. In the preferred construction the cavity is relatively deep and of predetermined capacity to hold the appropriate volume of allergen when filled to the rim. The cavity thus serves to standardize the volume of allergen applied to the skin.

For the convenience of the medical practitioner the allergy testing strips can be supplied in kit form, with each strip being marked to identify its respective allergen or allergens. The kit may also include control strips having no allergen applied to their lances. Use of the strips by the practitioner is convenient, as no instruments are required and as the strips are discarded after use.

BRIEF DESCRIPTION OF THE DRAWINGS

FIG. 1 is a bottom view of the test strip embodying the principles of the present invention;

FIG. 2 is a sectional veiw taken on the line 2—2 of FIG. 1;

FIG. 3 is a sectional view similar to FIG. 2 illustrating a second embodiment of a test strip; and FIG. 4 is a sectional view of a single-lance type of test strip.

The thickness of the layers in FIGS. 2, 3 and 4 is exaggerated for clarity of illustration.

DETAILED DESCRIPTION

FIGS. 1 and 2 illustrate an allergy test strip 10 which includes a strip of flexible adhesive tape in the form of a plastic strip 12 having on one surface a layer of pressure-sensitive adhesive 14. Preferably the strip 12 is clear, i.e., essentially colorless, and is sufficiently transparent that a skin reaction can be observed through it. The adhesive 14 is also essentially transparent and colorless. Projecting from the adhesive surface is a group of pointed or bladed lances 16 which carry an allergen (not illustrated) on their surfaces and/or in the interstices between them. The inner ends of the lances 16 are attached to a substrate 18 which in turn is attached to the film 12 by means of the adhesive layer 14. Preferably the substrate 18 is relatively rigid compared to the adhesive tape, although it can be flexible. A removable protective cover 20 overlies the group of lances 16 and is sealed in place at its periphery by contact with the adhesive layer 14. The cover 20 could alternatively be relatively rigid or elastic and held in place by frictional engagement with the periphery of the group of lances. A removable protective film 22 overlies the cover 18 and the exposed adhesive and is held in place by the latter. In the illustrated embodiment the test strip 10 is rectangular and the group of lances is circular, these being the preferred shapes.

FIG. 3 illustrates a similar allergy testing strip 10' which differs somewhat from the FIG. 1 device. In the FIG. 3 embodiment, the relatively rigid substrate 18' is concave outwardly to form a cavity or well for retaining liquid allergen. Also, there is a single removable film 22' which overlies both the group of lances and the exposed adhesive layer 14'.

To use the test strip 10 or 10' the medical practitioner first removes the protective elements 22, 20 or 22'. If the allergen is in liquid form no further preparation is required. If the allergen is in dry form the practitioner will apply several drops of sterile water to the group of lances 16 or 16' to dissolve or disperse the allergen and allow it to impregnate the spaces between the lances. After sterilizing the skin portion selected for the allergy test, the practitioner applies the adhesive side of the test strip 10 or 10' to the skin to hold the strip in place. Simultaneously or subsequently he gently and firmly presses with his fingers against the strip opposite the group of lances to cause the latter to penetrate the skin. The liquid allergen is thus carried partly into the skin and is maintained in constant contact with the traumatized skin cells until the strip is removed. A contact time of 15–20 minutes is generally suitable and upon removal of the strip the practitioner observes the punctured skin area to determine the extent of allergic reaction. The punctured skin area can be compared to an adjacent control area which has been punctured by the allergen-free lances of a control test strip.

FIG. 4 illustrates a test strip 30 which includes only a single lance 32 or a plurality of such lances spaced apart sufficiently that a skin reaction caused by one lance is independent of a skin reaction caused by another lance. In the illustrated construction the lance 32 is molded from plastics material integrally with a substrate 34 which forms a concave recess 36 around the base of the lance 32. The substrate 34 is circular in plan view and is dome-shaped with a peripheral flange 38 which surrounds the generally semi-spherical recess 36. The lance 32 projects through the center of the recess 36 and is conical in shape with a sharp point 40. Suitable dimensions for the substrate 34 are an overall diameter of about 0.3 inches, an overall height of about 0.125 inches and a flange and wall thickness of about 0.03 inches. The conical lance 32 may have a taper of 16°.

As with the embodiments of FIGS. 2 and 3 the test strip 30 of FIG. 4 includes a plastic strip 42, preferably essentially colorless and transparent, coated on its lower surface with a layer of pressure-sensitive adhesive 44. While not shown in FIG. 4 the test strip 30 can be provided with a protective film (as shown at 22 in FIG. 2 and at 22' in FIG. 3), and the lance 32 can be provided with a cover (as shown at 20 in FIG. 2). The concave substrate in FIG. 3 and recess 36 in FIG. 4 serve to standardize the amount of allergen applied to the skin.

What is claimed is:

1. A method for allery testing comprising: applying to the skin of a patient a test strip in the form of a thin, flexible essentially transparent strip of adhesive tape a portion of which carries on its adhesive side at least one skin-penetrating projecting lance device carrying an allergen, so that the tape releasably adheres to the skin, the lance device including a plate-like substrate having in one surface thereof an imperforate concave surface forming an open-ended cavity retaining liquid allergen therein and at least one lance projecting from said concave surface and having an outer end located outside said cavity; supplying said outer end with said allergen; and pressing at least said portion against the skin to cause the lance to penetrated the skin to a depth less than subcutaneous tissue thereby carrying a portion of the allergen into the skin and maintaining contact between the allergen and the thus-traumatized skin cells; leaving the strip in place for a period of time sufficient for the patient's skin, if allergic to the allergen, to produce an allergic reaction which can be observed through the strip.

2. A method as in claim 1 wherein there are a plurality of lances projecting from said concave surface and having outer ends located outside said cavity the interstices between the lances retaining liquid allergen.

3. A method as in claim 1 wherein said concave surface in one surface of the substrate is formed by a dome shaped protrusion on the opposite surface of said substrate.

4. A method as in claim 3 wherein said concave surface is generally semi-spherical and wherein said plate-like substrate forms a peripheral flange around said cavity.

5. A method as in claim 1 including applying and pressing against the skin of the patient a control strip of generally the same construction as said test strip, including the transparent strip, but without allergen associated with the lance; and leaving said control strip in place for about the same length of time as said test strip.

6. A method as in claim 1 wherein a plurality of the allergen-carrying test strips are applied to the patient's skin generally simultaneously, each such test strip carrying a different allergen.

7. A test strip for allergy testing comprising a flexible strip of essentially transparent tape having one of its surfaces coated with an adhesive so that said one surface can be releasably adhered to a patient's skin; a portion of said one surface carrying at least one lance device which includes a rigid substrate having an imperforate concave surface in one surface forming an open-ended cavity and at least one lance projecting from said concave surface to a point outside said cavity.

8. A test strip as in claim 7 including a removable protective cover overlying the lance.

9. A test strip as in claim 7 wherein said concave surface is formed by a dome-shaped protrusion on the opposite surface of said substrate.

10. A test strip as in claim 9 wherein said concave surface is generally semi-spherical and wherein said substrate forms a peripheral flange around the cavity.

11. A test strip as in claim 7 wherein there are a plurality of closely-spaced, allergen-carrying lances arranged in a group.

12. A test strip as in claim 11 wherein said lances are disposed in a circular group.

13. A lance device for use in allergy testing by a technique involving penetration of an allergen into the skin comprising a rigid plate-like substrate having an imperforate concave surface forming an open-ended cavity in one surface of the subtrate and forming a peripheral flange around the cavity, said cavity being adapted to retain a quantity of liquid allergen and at least one lance means projecting from said concave surface and extending to a location outside the cavity for penetrating the skin said lance means being adapted to carry the liquid allergen into the skin when said one surface of said substrate is pressed against the skin.

14. A lance device as in claim 13 wherein said lance is imperforate and conical.

15. A lance device as in claim 13 wherein said concave surface is formed by a dome-shaped protrusion on the opposite surface of said substrate.

16. A lance device as in claim 15 wherein said lance is imperforate and conical.

17. A lance device as in claim 15 wherein said concave surface is generally semi-spherical and wherein said plate-like substrate forms a flange around the cavity.

18. A lance device as in claim 17 wherein said lance is imperforate and conical.

19. A method for allergy testing comprising applying to the skin of a patient a lance device which comprises a rigid plate-like substrate having an imperforate concave surface forming a cavity in one surface of the substrate and forming a peripheral flange around the cavity, said cavity retaining a liquid allergen, and at least one lance projecting from said concave surface and extending to a location outside the cavity, supplying said lance with said allergen, pressing said one surface of said substrate against the skin so as to position the flange against the skin to cause the projecting lance to penetrate the skin to a depth less than the subcutaneous tissue thereby carrying the allergen into the skin and maintaining contact between the allergen and the thus-traumatized skin cells, leaving the lance device in place for a period of time sufficient for the patient's skin if allergic to the allergen, to produce an allergic reaction whereby the patient's allergy to the allergen may be determined by visual observation of the skin area penetrated by the lance.

* * * * *